(12) United States Patent
Norred

(10) Patent No.: US 6,482,228 B1
(45) Date of Patent: Nov. 19, 2002

(54) PERCUTANEOUS AORTIC VALVE REPLACEMENT

(76) Inventor: Troy R. Norred, 4511 Royal Lythem, Columbia, MO (US) 65203

( * ) Notice: Subject to any disclaimer, the term of this patent is extended or adjusted under 35 U.S.C. 154(b) by 0 days.

(21) Appl. No.: 09/712,121

(22) Filed: Nov. 14, 2000

(51) Int. Cl.[7] ................................................. A61F 2/06
(52) U.S. Cl. ..................................... 623/2.17; 623/1.24
(58) Field of Search ............................... 623/2.1, 2.12, 623/2.13, 2.14, 2.18, 2.2, 2.22, 2.17

(56) References Cited

U.S. PATENT DOCUMENTS

| | | | | |
|---|---|---|---|---|
| 4,787,901 A | * | 11/1988 | Baykut | 623/2.1 |
| 5,397,351 A | * | 3/1995 | Pavcnik | 623/2.1 |
| 5,413,599 A | * | 5/1995 | Imachi | 623/2.1 |
| 5,545,215 A | * | 8/1996 | Duran | 623/2.1 |
| 5,549,665 A | * | 8/1996 | Vesely | 623/2.1 |
| 5,891,195 A | * | 4/1999 | Klostermeyer | 623/2.1 |
| 5,957,949 A | * | 9/1999 | Leonhardt | 623/2.1 |
| 6,027,525 A | * | 2/2000 | Suh | 623/2.1 |
| 6,110,201 A | * | 8/2000 | Quijano | 623/2.1 |
| 6,168,614 B1 | * | 1/2001 | Anderson | 623/12.2 |
| 6,254,642 B1 | * | 7/2001 | Taylor | 623/12.2 |
| 6,264,700 B1 | * | 7/2001 | Kilcoyne | 623/12.2 |

* cited by examiner

*Primary Examiner*—Corrine McDermott
*Assistant Examiner*—William H Matthews
(74) *Attorney, Agent, or Firm*—Chase Law Firm, L.C.

(57) ABSTRACT

An aortic heart valve which is adapted to be placed percutaneously without the need for open-heart surgery is placed by a catheter and held in place with a stent system. The stent system is expanded in the ascending aorta to anchor the valve in the aortic channel above the native aortic valve.

24 Claims, 7 Drawing Sheets

PERCUTANEOUS AORTIC VALVE REPLACEMENT

BACKGROUND OF THE INVENTION

This invention relates to aortic heart valves and, in particular, to a percutaneous aortic heart valve that is placed by a catheter or other means and held in place with a stent system without the need for surgery.

The aortic valve undergoes a series of changes based upon the initial structure at birth and the normal dynamic daily stresses. The trileaflet aortic valve normally will not become stenotic until the seventh decade of a person's life unless infectious processes are introduced earlier. The incidence of aortic stenosis can reach between two and nine percent of the people in this age range. The average mortality rate at all ages is nine percent a year which also increases as a population ages. Coupled with these facts is the likelihood that as a person ages and becomes symptomatic with aortic stenosis, he is less likely to be an operative candidate due to being physically unable to withstand the stresses of surgery. The mortality of octogenarians has been reported as high as 20% for aortic valve replacement which can preclude a reasonable attempt at the therapy of choice, e.g., surgical replacement of the aortic valve using the traditional method of open heart surgery.

It is therefore the primary object of the present invention to provide an aortic valve that can be placed nonsurgically.

Another object of the present invention as aforesaid is to provide an aortic valve which may be anchored in the ascending aorta by a stent system.

Yet another important object of the present invention is to provide an aortic valve as aforesaid which may be placed percutaneously.

Still another object of the present invention is to provide an aortic valve as aforesaid which functions without removal of the native aortic valve.

Another important object of the present invention is to provide an aortic valve as aforesaid which reduces regurgitation of a native aortic valve.

Yet another important object of the present invention is to provide an aortic valve as aforesaid which increases the effective aortic valve orifice area while minimizing the resultant aortic regurgitation.

Still another important object of the present invention is to provide an aortic valve as aforesaid which reduces left ventricle energy expenditure from aortic regurgitation.

Yet another important object of the present invention is to provide an aortic valve as aforesaid which reduces long-term ventricular and aortic sequelae from pressure overload caused by aortic regurgitation.

Another important object of the present invention is to provide an aortic valve as aforesaid which can be placed nonsurgically so as to minimize the health risk to a patient during the procedure.

These and other objects and advantages of this invention are achieved by an artificial biomechanical aortic valve integrated with a stent system, which may be placed nonsurgically so as to minimize the risk to the patient during the procedure. The aortic valve is anchored in the ascending aorta with further support supplied in branch vessels or descending aorta as necessary due to the stress forces placed on the artificial valve by the normal hemodynamic pressures in the aorta. The valve is connected to the stent system by serially connected rods. Because of the relatively large surface area of the stent system, this design displaces the forces placed upon the artificial valve across this large surface area. Placing the device nonsurgically eliminates the need for a bypass pump or sternotomy and the associated postoperative risks.

These and other objects and advantages of this invention will become apparent from the following description taken in connection with the accompanying drawings, wherein is set forth by way of illustration and example, a now preferred embodiment of this invention.

DESCRIPTION OF THE PREFERRED EMBODIMENT

Figure 1:
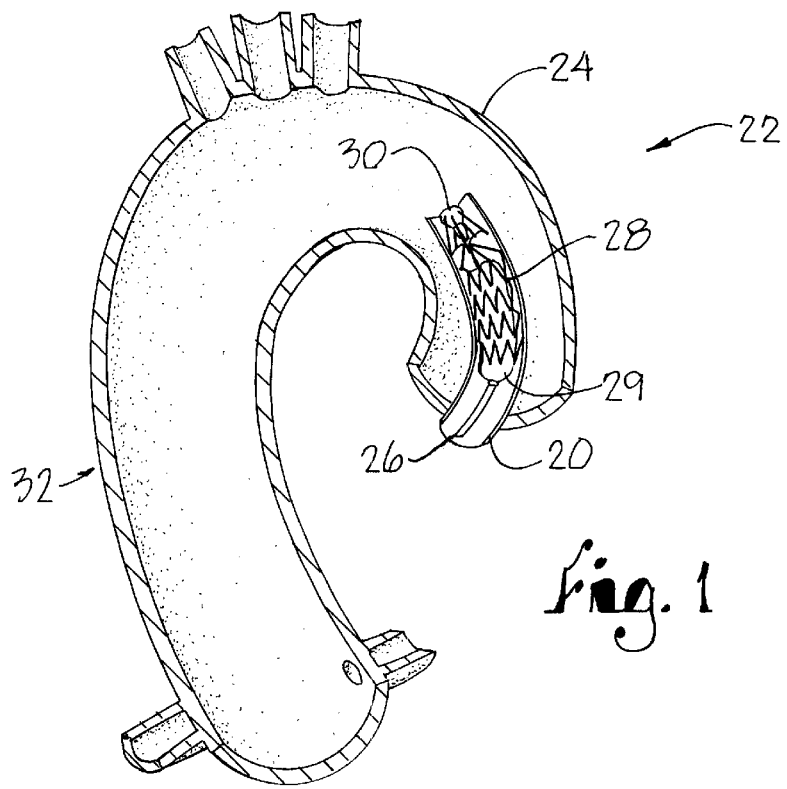
FIG. 1 is a diagrammatic sectional view of a catheter containing aortic valve and stents of the present invention in the descending portion of an aorta.

Turning more particularly to the drawings, FIG. 1 illustrates a sectional diagrammatic view of a cannular catheter 20 in the descending portion 22 of aorta 24. Cannular catheter 20 contains a balloon catheter 26 which is surrounded by a wire mesh tube or stent system 28 connected to artificial valve 30.

Figure 2:
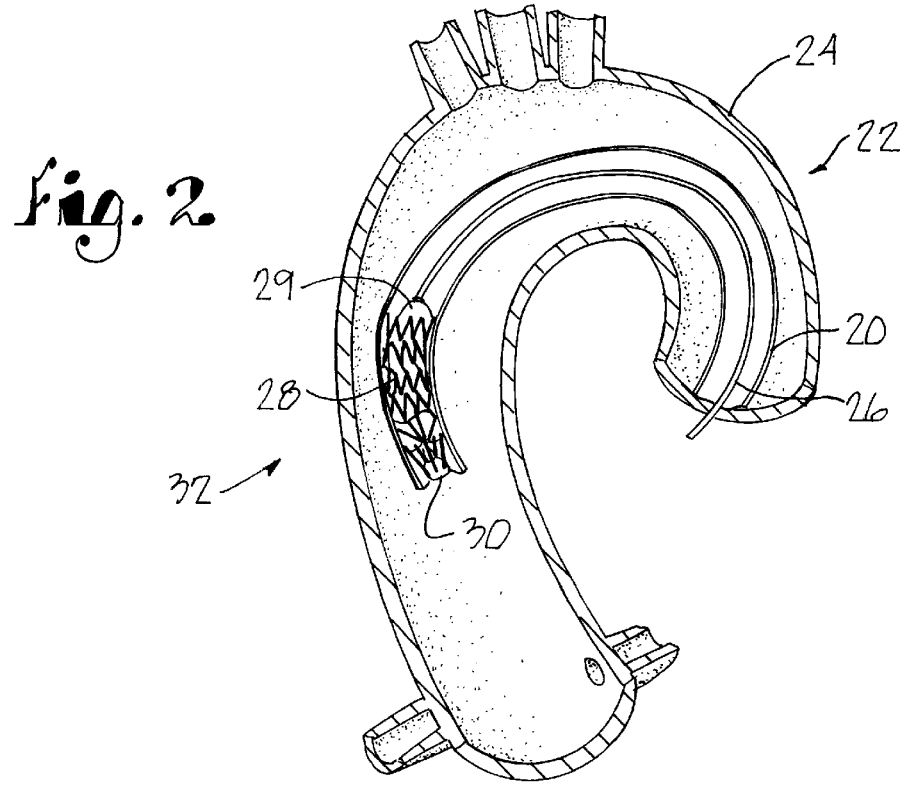
FIG. 2 is a diagrammatic view of FIG. 1 with the catheter advanced to the ascending portion of the aorta.

The stent system 28 is made up of a small slotted stainless steel tube or series of interconnected rods which form an expandable cylindrical lattice or scaffolding. The stent system 28 is initially collapsed to a small diameter around an angioplasty balloon 29 so that it and valve 30 may be guided into place using an antegrade approach through the fermoral artery (not shown) to the ascending aorta 32 (FIG. 2).

Figure 3:
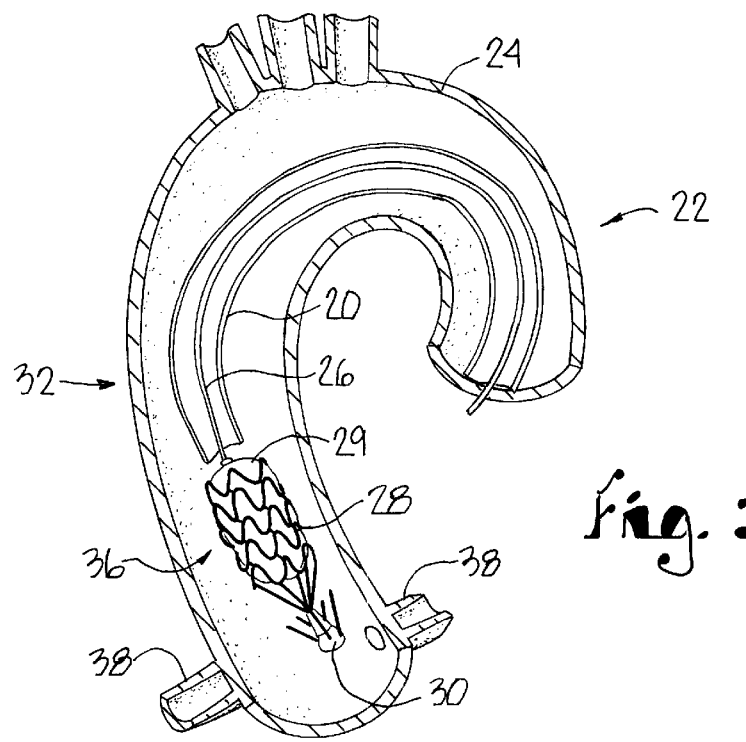
FIG. 3 is a diagrammatic view of FIG. 2 with the aortic valve and stents being deployed into the aorta and the stents being expanded by inflation of a balloon.

Once cannular catheter 20 is located in ascending aorta 32 above native aortic valve 34, the balloon catheter 26 is deployed (FIG. 3) to place the valve/stent combination 36 in the correct anatomical position so that valve 30 is above aortic valve 34 (FIG. 4) and below coronary arteries 38 so that the openings to coronary arteries 38 are unobstructed. When the valve/stent combination 36 is correctly placed, the balloon 29 is inflated to expand the stent scaffolding 28 and force the stent system 28 against the inner walls of ascending aorta 32 to anchor valve 30 in place. After balloon 29 is deflated and balloon catheter 26 is removed, the stent 28 remains locked in place. The stent lattice 28 may extend into descending aorta 32 or branch vessels (not shown) to further support and secure valve 30 in place.

Once the valve and stent combination 36 is in place, the balloon 29 is deflated and balloon catheter 26 is retracted into cannular catheter 20. Both catheters 26 and 20 are removed from aorta 24 through the fermoral artery (not shown).

Figure 5:
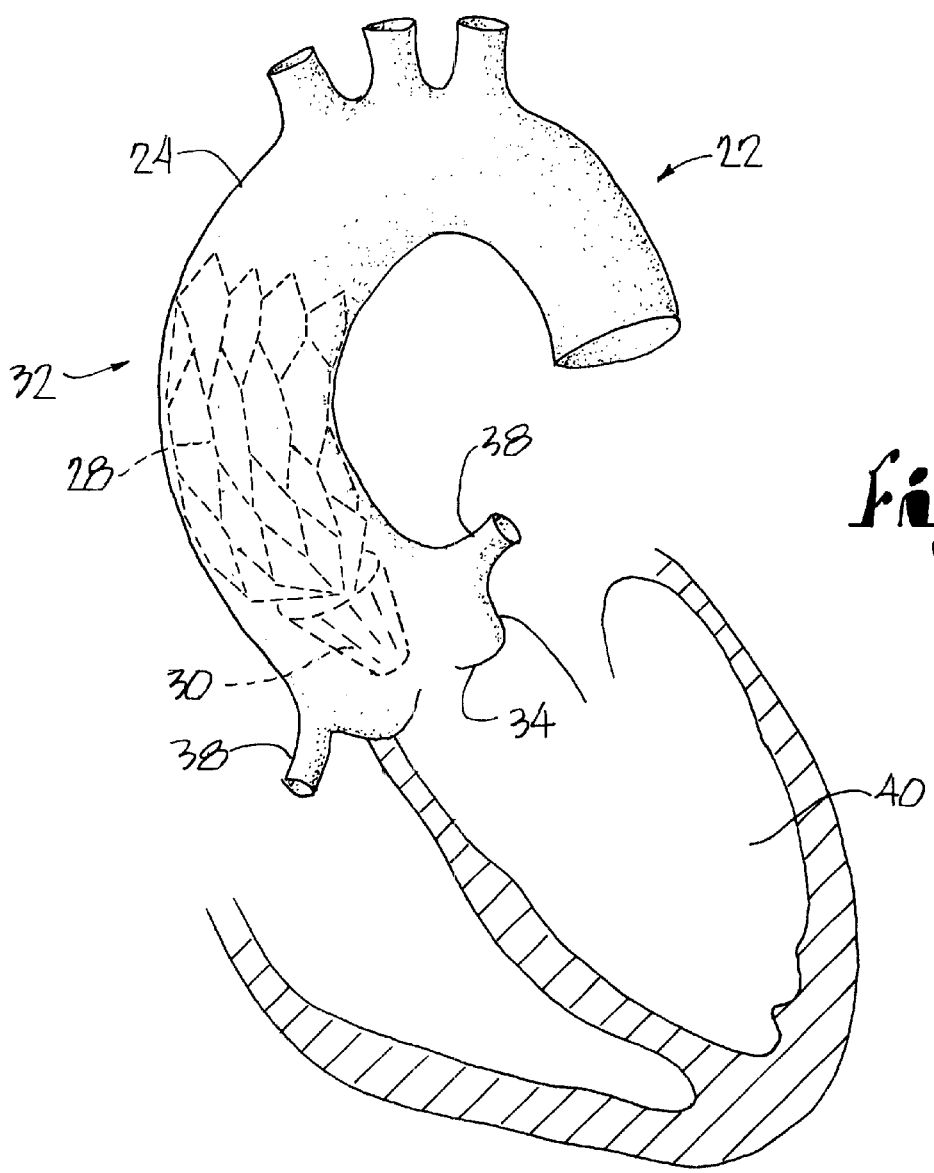
FIG. 5 is a diagrammatic view of FIG. 4 showing the relationship between the placement of the stent system and valve to the aortic valve and left ventricle.
Figure 6:
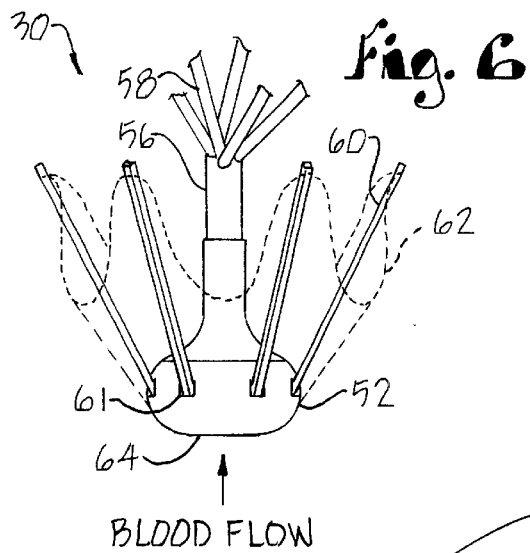
FIG. 6 is an umbrella aortic valve in a closed position.

Simultaneously with placement of the valve/stent combination 36, the fermoral vein would be accessed and cannulated to guide a balloon catheter into the left ventricle using a retrograde approach to perform a valvoplasty by inflating the balloon within the aortic valve. The purpose of the valvoplasty is to force the aortic valve open to relieve the pressure gradient between the left ventricle 40 (FIG. 5) and aorta 24. Visualization to place the catheters within the aorta 24 and left ventricle 40 would be accomplished using continuous roentgenogram and ultrasound techniques, such as intracardiac echocardiography (ICE) or fluoroscopy, which are known in the art.

Use of this valve/stent combination 36 precludes removal of the native aortic valve 34. The focus would instead be upon debulking of the native aortic valve 34. The main purpose is abolition of the resting gradient. The techniques employed would attempt to achieve a large effective aortic valve area regardless of the functioning of the native aortic valve 34 post-procedure because an artificial aortic valve 30 designed to prevent aortic regurgitation would be in place. Aortic valve 30 is designed not to hinder the ejection of blood from the left ventricle, and to minimize the aortic regurgitant volume. The techniques used to debulk the native aortic valve may include positioning of an Er-YSGG percutaneous laser to decalcify the valve and repeat balloon aortic valvuloplasty. If this is not effective then high frequency ultrasound percutaneously applied to the aortic valve may be necessary.

These techniques have been shown to be highly effective at producing debulking and preventing restenosis and increasing the effective aortic valve orifice area. However, they produce tremendous aortic regurgitation. This would not be a problem for the unattached valve 30 which would work as disclosed below for aortic regurgitation.

If these techniques do not produce the desired result of increasing the effective aortic valve orifice area then a host of options are still available. For example, two rings may be guided onto both the aortic and ventricular sides of the native aortic valve and pneumatically sealed together. Then expandable and retractable biotomes may be percutaneously placed for controlled dissection of the native aortic valve. The biotomes may be used for primary resection without stabilizing rings, but there would need to be a stabilization mechanism for the native aortic valve. Another such mechanism could employ the use of a micro screw into the native valve, which would act as an anchor to guide a biotome onto the native valve. Then the biotomes would take small snips in a controlled fashion off of the native valve. This would gradually increase the effective orifice area. Because the artificial valve is not anchored or dependent upon the native valve for its function, this technique could be easily reapplied, if the native valve were to restenose, without comprising the artificial valve. A tremendous advantage of this procedure would be its independence from a need for a percutaneous bypass pump.

Referring to FIGS. 6–9, an inverted generally umbrella-shaped valve 30 is shown. Umbrella valve 30 has a generally pear or bulb-shaped main body 52 and a neck 54 which extends from the body. Extending from neck 54 is connecting rod 56 which secures stent struts 58 to umbrella valve 30. Frame members or ribs 60 extend radially from and are hingedly attached to body 52. Hinges 61 permit ribs 60 to move between a folded position (FIGS. 6–7) where the ribs extend generally parallel to neck 54, and an unfolded position (FIGS. 8–9) where the ribs extend generally radially from an perpendicular to body 52. Hinges 61 prevent ribs 60 from overextending when unfolded. A generally circular canopy 62 is secured to the lower sides of each of the frame members 60 and the lower side 64 of body 52. Canopy 62 may be made of a biocompatible, flexible material such as an elastomeric sheet or a Dacron® reinforced polymer, for example. Frame members 60 may be made of stainless steel or a plastic polymer that is able to withstand the shear stresses during folding of valve 30.

Figure 8:
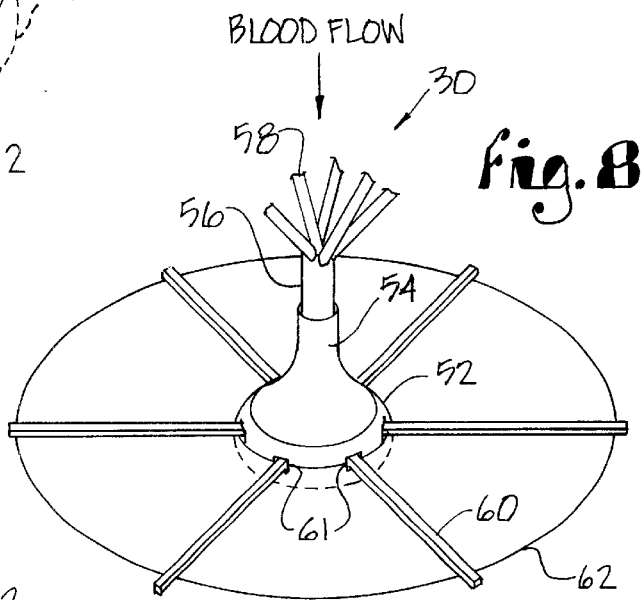
FIG. 8 is the umbrella aortic valve of FIG. 5 in an open position.
Figure 7:
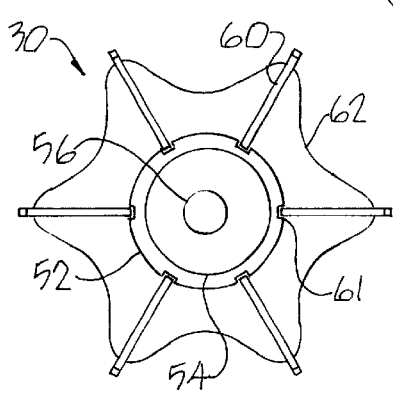
FIG. 7 is a plan view of the umbrella aortic valve of FIG. 5.
Figure 9:
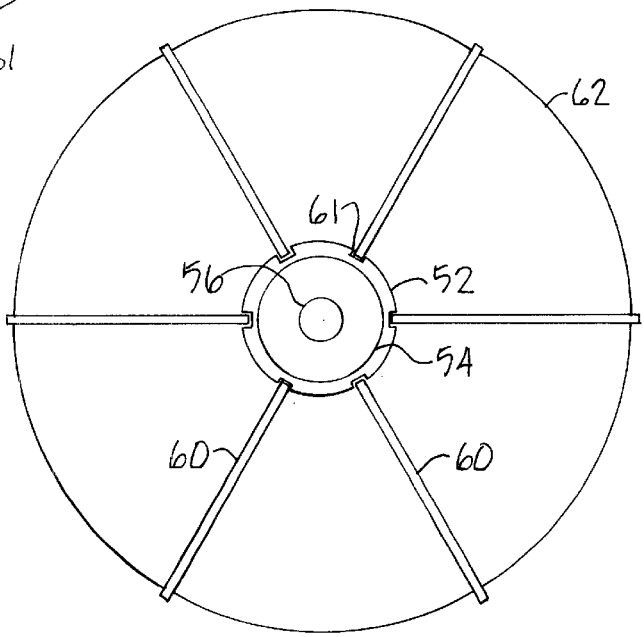
FIG. 9 is a plan view of the umbrella aortic valve of FIG. 7.
Figure 10:
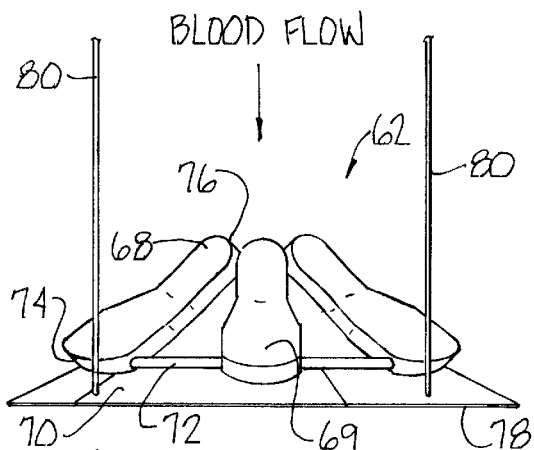
FIG. 10 is a diagrammatic view of a cone-shaped aortic valve in a closed position.

In FIGS. 6–9 frame members 60 are shown generally straight. However, frame members 60 may be curved inwardly toward neck 54 when valve 30 is in the folded or collapsed position (FIG. 6) and generally tangentially to the inner wall of the aorta and toward the stent system 28 (FIG. 4) when valve 30 is in the unfolded position (FIG. 8). Additionally, canopy 62 may extend beyond the ends of frame members 60 to help reduce or eliminate peri-valvular leaks by sealing the valve against the inner wall of the aorta.

The end 64 of valve body 52 is generally hemispherical which permits the desired laminar blood flow characteristics of the native aortic valve in the aorta around valve 30. Generally, any rounded shape, such as a rounded cone or hemi-ellipse, will produce satisfactory laminar flow.

Figure 4:
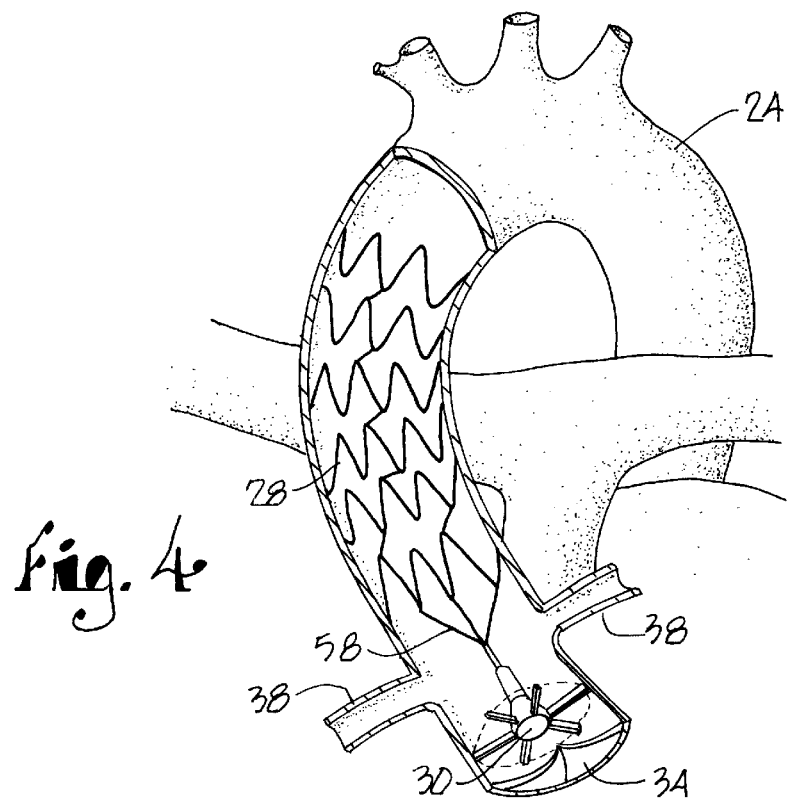
FIG. 4 is a diagrammatic view of FIG. 3 with the stents expended and in place and the catheter removed.

Generally, umbrella-shaped valve 30 is placed in a position above the native aortic valve and below the openings of the coronary arteries 28 (FIG. 4). The structure of valve 30 collapses to a folded (FIG. 6) position wherein the ribs extend along the neck such that the canopy does not traverse the aortic channel. Thus, during systolic contraction of the left ventricle the blood from the left ventricle may be expelled unimpeded into the aorta (FIGS. 6–7) as the valve is folded. During diastolic filling of the left ventricle, the pressure in the aorta becomes greater than the pressure in the left ventricle and the blood attempts to flow from the aorta into the left ventricle or regurgitate. This backflow is caught in the canopy 62 which causes valve structure 30 to unfold (FIGS. 8–9) and prevents aortic regurgitation as the opening between the aorta 24 and the left ventricle is sealed. At this position ribs 60 extend radially and generally perpendicular from body 52.

Referring to FIGS. 10–13 a second embodiment of an artificial aortic valve is shown which may be placed percutaneously. Conical valve 66 consists of two to 32 interconnected plates or fingers 68 and a generally ring-shaped base 70 and a ring 72 secured to the base 70. The fingers 68 are generally wedge or bowling pin-shaped and are hingedly secured together by ring 72 extending through the base 74 of each finger 68 and interconnected by a biocompatible, durable, flexible generally conically-shaped fabric 75 membrane secured to the inside surfaces 69 of the fingers. The fingers 68 extend generally radially inwardly and away from the base 70. Fingers 68 may be constructed of stainless steel, plastic or other biocompatible material.

In the closed position (FIGS. 10–11), the tops 76 of the fingers contact each adjacent fingertip 76 to prevent regurgitation. It should be understood that if the number of fingers is increased, contact with the adjacent fingers may be along the entire length of the finger 68. If contact is along the entire side length of each adjacent finger when conical valve 66 is in the closed position, a membrane 75 may not be necessary to prevent regurgitation. To minimize components and to aid in miniaturizing the device for delivery, the number of fingers 68 may be reduced to two to four interconnecting fingers 68.

Figure 12:
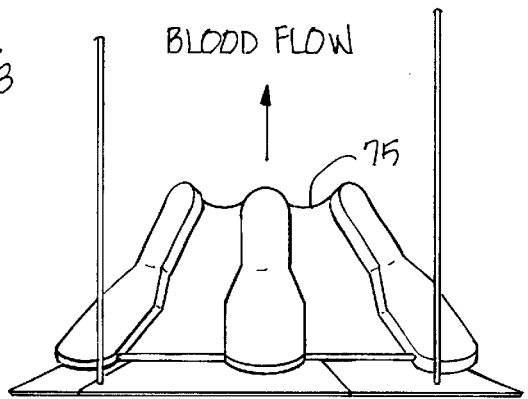
FIG. 12 is the cone-shaped valve of FIG. 10 in an open position.
Figure 11:
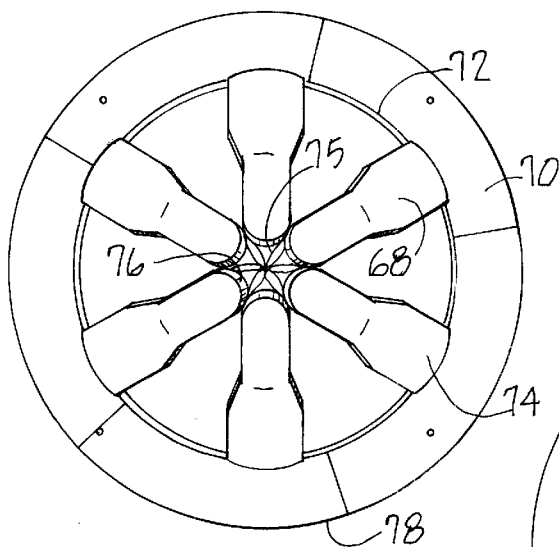
FIG. 11 is a plan view of the cone-shaped valve of FIG. 10.
Figure 13:
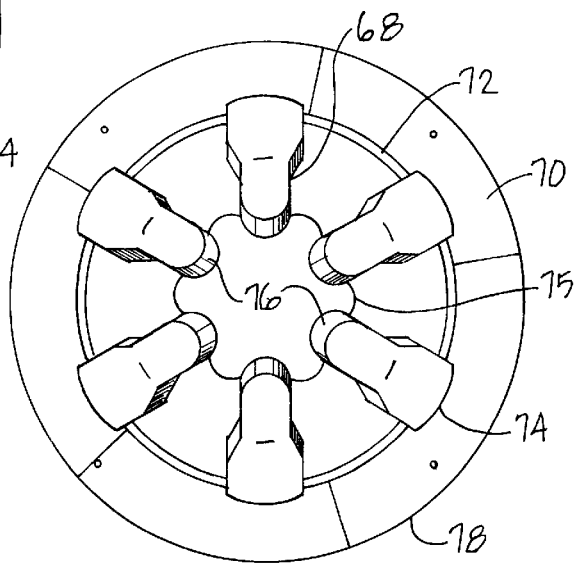
FIG. 13 is a plan view of the cone-shaped valve of FIG. 12.

During systole valve 66 expands or opens as shown in FIGS. 12–13 to allow blood ejected from the left ventricle to flow through the center of valve 66. Fingers 68 pivot on ring 72 and tips 76 separate to allow blood to flow through the center of valve 66. Membrane 75 prevents fingers from overextending to block coronary arteries 38 (FIG. 4).

Valve 66 and the combined stent 28 is guided into position as shown in FIGS. 1–4, and placed over the native aortic valve 34. Base 70 is seated against the root of the aortic valve 34 next to the inner wall of the aorta 24 below coronary arteries 38. The rim 78 of base 70 is made of a pliable biocompatible material which seals against the root of the native aortic valve 34 to reduce peri-valvular leaks. Valve 66 is anchored along the root of the aortic valve with connecting rods 80 which are connected to the ascending aortic stents 28 (see FIG. 4). Valve 66 is placed such that rods 80 are positioned between the right and left coronary ostia tangentially along the sinus of valsalva. In this embodiment, there are no intraluminal connecting rods 58 within the ascending aorta as with umbrella valve 30 (see FIG. 4).

Conical valve 66 centralizes the blood ejection jet from the left ventricle providing improved laminar flow characteristics through the valve 66 and minimizes hematologic sequelae.

Referring to FIGS. 14–17, a third embodiment of an artificial aortic valve is shown which may be placed percutaneously. Trihedral valve 82 is similar in structure and operation to conical valve 66 (FIGS. 10–13). Arms 84 are hingedly attached to ring 86 of base 88 and extend upwardly and radially inwardly from base 88 to generally form a trihedron or cone. Each rod 84 has a crescent-shaped pad 90 at its free end. A cone-shaped membrane 92 of fibrous polymer is secured to each arm 84 and base 88 (not shown in FIG. 14).

Figure 14:
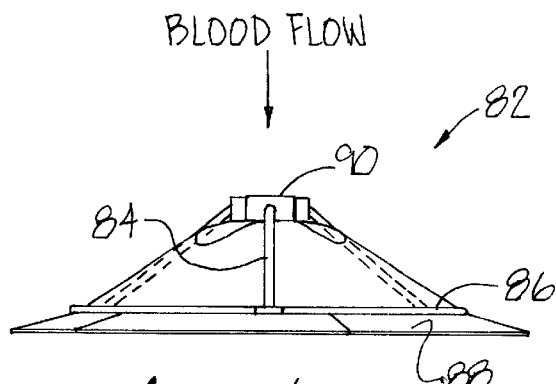
FIG. 14 is a diagrammatic view of another cone-shaped aortic valve in a closed position.
Figure 16:
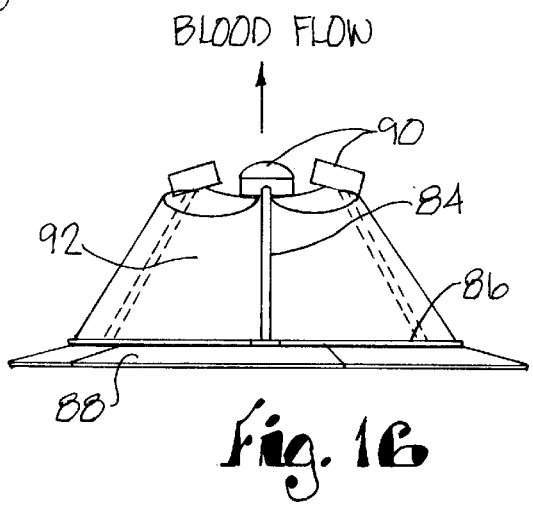
FIG. 16 is the cone-shaped aortic valve of FIG. 14 in an open position.
Figure 15:
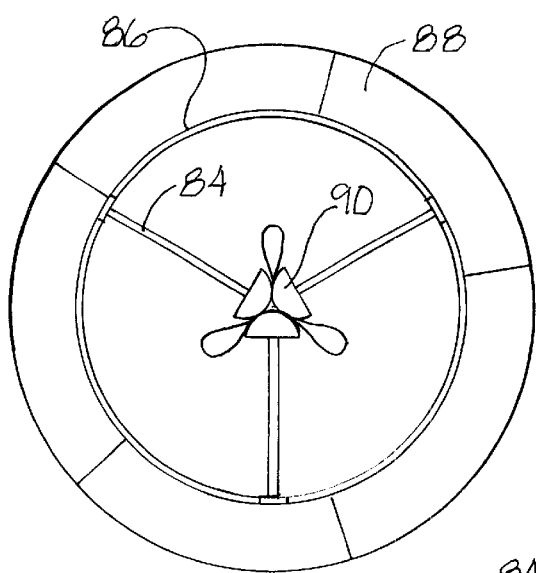
FIG. 15 is a plan view of the cone-shaped valve of FIG. 14.
Figure 17:
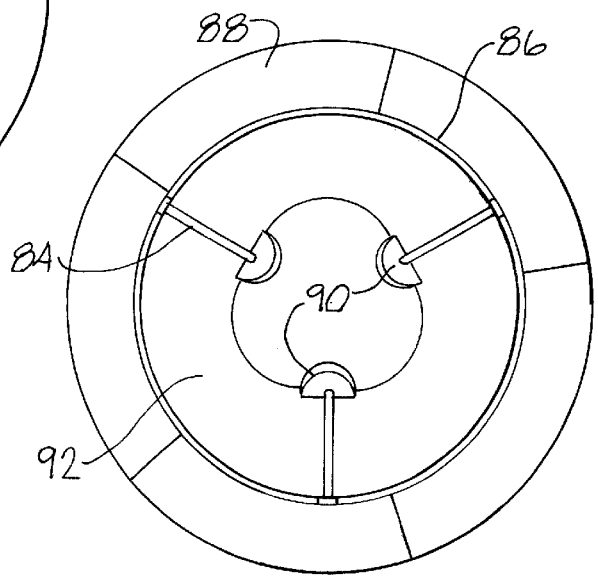
FIG. 17 is a plan view of the cone-shaped valve of FIG. 16.

During diastole, back flow of blood from the aorta to the left ventricle causes valve 82 to close preventing regurgitation (FIGS. 14–15). During systole, blood is ejected from the left ventricle to force valve 82 open and allow blood to flow into the ascending aorta through the center of valve 82. Valve 82 is anchored along the aortic valve root wall with connecting rods (not shown; see connecting rods 80, FIG. 10) which are connected to ascending aortic stents 28 (FIG. 4). Valve 82 is placed so that the connecting rods are positioned between the right and left coronary ostia tangentially along the sinus of valsalva. In this embodiment, as in the conical valve 66, there are no interluminal connecting rods 58 within the ascending aorta as with umbrella valve 30 (see FIG. 4).

Base 88 of valve 82 is constructed as disclosed above for base 70 of conical valve 62. Arms 84 may be constructed of stainless steel or other structural biocompatible material such as plastic. Crescent-shaped pads 90 may be constructed of stainless steel for durability or of softer biocompatible materials to better seal the valve 82 when in the closed position (FIGS. 14–15), and reduce regurgitation.

Figure 18:
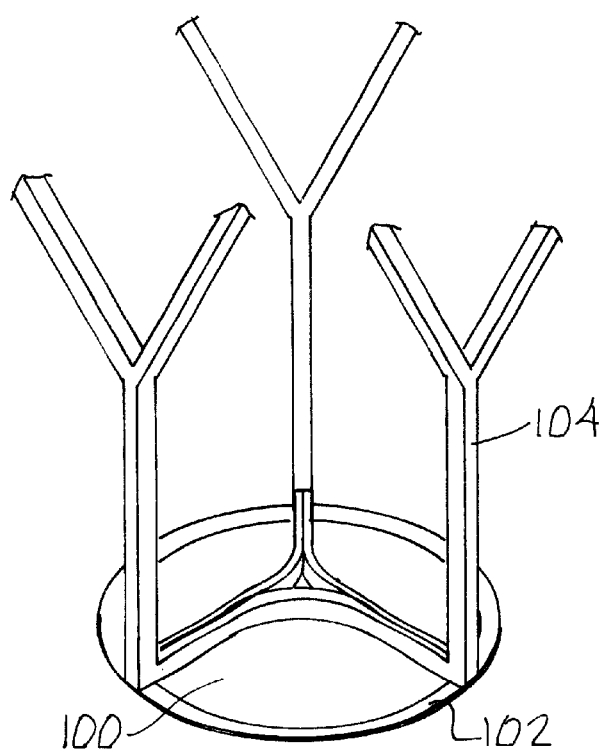
FIG. 18 is a diagrammatic view of a cadaver/porcine incorporated valve and stent system.
Figure 19:
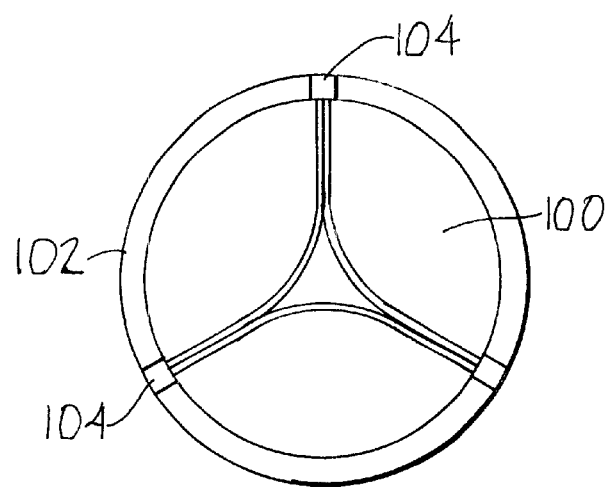
FIG. 19 is a plan view of the cadaver/porcine valve of FIG. 18.

Other valvular designs which may prove valuable to this technique include the usage of biological tissue incorporated valves, such as cadaver/porcine valves, placed within a percutaneously stented system the benefits of favorable flow and hematologic characteristics (see FIGS. 18 and 19).

Cadaver/porcine valve 100 is retained in a base ring 102. Ring 102 is made of a pliable biocompatible material which seals against the root of the native aortic valve 34 (see FIG. 4) to reduce peri-valvular leaks. Valve 100 is anchored along the root of the aortic valve with connecting rods 104 which are connected to the ascending aortic stents 28 shown in FIG. 4. Valve 100 is placed such that rods 104 are positioned between the right and left coronary ostia tangentially along the sinus of valsalva.

The central themes involve increasing the effective aortic valve orifice area while minimizing the resultant aortic regurgitation. Thus, the goals in reducing left ventricular energy expenditure and its resultant long-term sequelae of pressure overload would be met with this system of percutaneously delivered aortic valves.

Having thus described the invention, what is claimed as new and desired to be secured by Letters Patent is:

1. An aortic valve for regulating blood flow through a channel of an aorta, the channel surrounded by an aortic wall, upon placement therein, said valve comprising:
   a body member having a configuration adapted to fit within a channel of an aorta;
   a membrane made of a material impervious to an aortic blood flow, said membrane having a first membrane position precluding a blood flow through the aorta and a second position for allowing a blood flow through the aorta; and
   a plurality of frame members with said membrane mounted thereto, each frame member having a first end pivotally secured to said body member and a second end, said frame members pivotally responsive to a condition within the aorta between a first position wherein said membrane at said first frame member position is at said first membrane position and a said second frame member position wherein said membrane is at said second membrane position.

2. An aortic valve as claimed in claim 1 wherein said membrane extends across the aortic channel to block a blood flow at said first membrane position and extends generally along the aortic channel to allow a blood flow through the aorta at said second membrane position.

3. The aortic valve as claimed in claim 1 further comprising means for stopping pivotal movement of said second end of said frame members into contact with the aorta wall.

4. The aortic valve as claimed in claim 1 wherein said condition within the aorta is a change in blood pressure in the aorta.

5. The aortic valve as claimed in claim 1 wherein said frame members and membrane move to said second positions in response to systolic ejection of blood from the left ventricle in which the blood pressure in the left ventricle is higher than the blood pressure in the aorta.

6. The aortic valve as claimed in claim 1 wherein said frame member and membrane move to said first position in response to diastolic filling of the left ventricle and the blood pressure in the aorta is higher than the blood pressure in the left ventricle resulting in a reverse flow of blood from the aorta to the left ventricle which is stopped by said membrane at said first position.

7. An aortic valve as claimed in claim 1 wherein said body member has an exterior configuration to present a space between said body member exterior configuration and the aortic wall to allow blood flow therearound at said membrane second position.

8. The aortic valve as claimed in claim 1 wherein said body member comprises a base presenting an edge adapted to seat about the aortic wall surrounding the aortic channel;
   an aperture in said base for blood flow therethrough;
   a ring surrounding said aperture, said first end of said frame members pivotally mounted to said ring with said membrane mounted thereto, said second ends of said frame members being in contact at said first frame member position to cause said membrane to span said base aperture and preclude a blood flow past said second frame member ends and said membrane, said frame members pivotable about said ring to a second position wherein said second frame member ends are displaced one from the other to allow a blood flow through the aperture and past said membrane.

9. The aortic valve as claimed in claim 8 wherein said membrane presents a base opening secured about said aperture and a free end having an aperture therein, said aperture in said free end of said membrane at said second frame and membrane positions is open to allow blood to flow though said membrane between said membrane base opening and said aperture in said free end of said membrane at said membrane second position.

10. The aortic valve as claimed in claim 9 wherein said membrane free end aperture is closed at said first frame membrane and member positions to preclude blood from flowing though said membrane at said membrane first position.

11. The aortic valve as claimed in claim 1 further comprising means for maintaining said body member within the aortic channel.

12. An aortic valve for regulating blood flow through a channel of an aorta upon placement therein, said valve comprising:

a body member having a configuration adapted to fit within a channel of an aorta to allow passage of a blood flow therearound;

a membrane for traversing the aortic channel to preclude blood flow therethrough; and at least two ribs for attachment of said membrane thereto, each rib having a first end hingedly attached to said body member and a free end extending from said body member, wherein said at least two ribs are responsive to a change in pressure in the aorta for movement between a first position wherein said membrane is unfolded so as to traverse the aortic channel and preclude a blood flow therethrough and a second collapsed position wherein said membrane is positioned relative to the aorta channel to allow a blood flow therearound.

13. The aortic valve as claimed in claim 12 wherein said at least two ribs extend radially from said body so as to traverse the aortic channel at a first rib position, said first rib position corresponding to unfold said membrane at said first position, and wherein said ribs extend generally along said aortic channel at a second rib position to collapse said membrane at said second position.

14. The aortic valve as claimed in claim 13 wherein said membrane presents an edge adapted for contact about a wall of the aortic channel in said first position, said contact seats said membrane edge against the aortic channel wall to reduce a blood flow therearound.

15. The aortic valve as claimed in claim 12 further comprising means for maintaining said body member at a selected position in the aorta.

16. An aortic valve for regulating a blood flow through an aortic channel surrounded by an aortic wall upon placement therein, said valve comprising:

a ring member having a circumference adapted to seat about an aortic wall surrounding an aortic channel, said ring including an aperture for blood flow therethrough;

a membrane having first and second spaced-apart open ends, said membrane made of a material resistant to a fluid flow therethrough; and means for mounting said first open end of said membrane about said ring aperture with said second open end displaced therefrom, said means moving said membrane second end between a first open position to allow a blood flow therethrough and a second closed position to preclude a blood flow therethrough.

17. The aortic valve as claimed in claim 16 wherein said mounting means comprises at least one arm having a first end hingedly secured to said ring member and a free end spaced therefrom, said first end of said at least one arm secured to said first end of said membrane, said free end of said at least one arm secured to said second end of said membrane, said at least one arm responsive to a blood flow within the channel for movement with said membrane between said first open and second closed positions.

18. The aortic valve as claimed in claim 17 wherein said at least one arm extends generally along a path of said blood flow at said first open position, and generally traverses a blood flow path when at said second closed position.

19. The aortic valve as claimed in claim 16 further comprising means for maintaining said ring member in said seat about the aortic wall.

20. An aortic valve for controlling a blood flow through an aortic channel upon placement therein, said valve comprising:

a tissue valve having an interior member made of a tissue material and presenting an opening movable between open and closed positions;

a ring member surrounding said tissue valve, said ring member having an outer circumference adapted to seat said ring member about an aortic wall surrounding an aortic channel;

means for maintaining said ring member in said seated position about the aortic wall, said tissue valve interior member responsive to changes of conditions within the aorta for movement of said opening between a first closed position and a second open position.

21. The aortic valve as claimed in claim 20 wherein said tissue valve interior member is responsive to changes in blood pressure in the aorta whereby to move said tissue valve between said first and second positions.

22. The aortic valve as claimed in claim 21 wherein said tissue valve interior member moves to said second position in response to systolic ejection of blood from the left ventricle in which the blood pressure in the left ventricle is greater than the blood pressure in the aortic channel.

23. The aortic valve as claimed in claim 21 wherein said tissue valve interior member moves to said first position in response to diastolic filling of the left ventricle whereby the blood pressure in the aortic channel is greater than the blood pressure in the left ventricle.

24. The aortic valve as claimed in claim 20 wherein said ring member contacts the wall of the aortic channel and seals said ring against the aortic channel wall to reduce blood flow therearound.

* * * * *

UNITED STATES PATENT AND TRADEMARK OFFICE
CERTIFICATE OF CORRECTION

PATENT NO.   : 6,482,228 B1
DATED        : November 19, 2002
INVENTOR(S)  : Troy R. Norred It is certified that error appears in the above-identified patent and that said Letters Patent is hereby corrected as shown below:

<u>Column 7,</u>
Lines 15 and 21, delete "though" and substitute -- through --.

Signed and Sealed this

Fourth Day of March, 2003

JAMES E. ROGAN
*Director of the United States Patent and Trademark Office*